(12) United States Patent
Hejazi

(10) Patent No.: US 12,225,937 B2
(45) Date of Patent: Feb. 18, 2025

(54) AEROSOL DELIVERY DEVICE WITH DOWNSTREAM FLAVOR CARTRIDGE

(71) Applicant: RAI Strategic Holdings, Inc., Winston-Salem, NC (US)

(72) Inventor: Vahid Hejazi, Winston-Salem, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 362 days.

(21) Appl. No.: 17/578,665

(22) Filed: Jan. 19, 2022

(65) Prior Publication Data

US 2022/0133369 A1   May 5, 2022

Related U.S. Application Data

(63) Continuation of application No. 16/708,785, filed on Dec. 10, 2019, now Pat. No. 11,259,569.

(51) Int. Cl.
*A24F 40/42* (2020.01)
*A24F 40/30* (2020.01)
(Continued)

(52) U.S. Cl.
CPC ............. *A24F 40/42* (2020.01); *A24F 40/30* (2020.01); *A61B 17/80* (2013.01); *A61B 90/94* (2016.02); *A24F 40/20* (2020.01); *A61B 50/30* (2016.02); *A61B 2090/037* (2016.02); *A61B 2090/061* (2016.02); *A61B 2090/3937* (2016.02)

(58) Field of Classification Search
None
See application file for complete search history.

(56) References Cited

U.S. PATENT DOCUMENTS

| | | |
|---|---|---|
| 2,057,353 A | 10/1936 | Whittemore, Jr. |
| 2,104,266 A | 1/1938 | McCormick |

(Continued)

FOREIGN PATENT DOCUMENTS

| | | |
|---|---|---|
| CN | 1541577 | 11/2004 |
| CN | 2719043 | 8/2005 |

(Continued)

OTHER PUBLICATIONS

International Preliminary Report on Patentability from the International Search Authority for PCT/IB2020/061709 mailed Jun. 23, 2022.

(Continued)

*Primary Examiner* — James Harvey
(74) *Attorney, Agent, or Firm* — Womble Bond Dickinson (US) LLP

(57) ABSTRACT

The present disclosure relates to a flavor delivery device and a cartridge that includes such flavor delivery device. The flavor delivery device includes a flavor substrate that can be formed of a porous material, and further including flavor material included within the flavor substrate. The flavor substrate is surrounded by an outer sleeve which is impermeable to the flavor material. The flavor delivery device may be positioned within a cartridge of an aerosol delivery device where the flavor delivery device is located downstream from a reservoir containing an aerosol precursor composition relative to the mouthend of the cartridge.

16 Claims, 8 Drawing Sheets

(51) Int. Cl.
  *A61B 17/80*   (2006.01)
  *A61B 90/94*   (2016.01)
  *A24F 40/20*   (2020.01)
  *A61B 50/30*   (2016.01)
  *A61B 90/00*   (2016.01)

(56) References Cited

U.S. PATENT DOCUMENTS

| | | |
|---|---|---|
| 3,200,819 A | 8/1965 | Gilbert |
| 4,922,901 A | 5/1990 | Brooks et al. |
| 5,060,671 A | 10/1991 | Counts et al. |
| 5,093,894 A | 3/1992 | Deevi et al. |
| 5,261,424 A | 11/1993 | Sprinkel, Jr. |
| 5,388,574 A | 2/1995 | Ingebrethsen et al. |
| 5,530,225 A | 6/1996 | Hajaligol |
| 5,687,746 A | 11/1997 | Rose et al. |
| 5,726,421 A | 3/1998 | Fleischhauer et al. |
| 5,865,185 A | 2/1999 | Collins et al. |
| 5,894,841 A | 4/1999 | Voges |
| 6,125,853 A | 10/2000 | Susa et al. |
| 6,155,268 A | 12/2000 | Takeuchi |
| 7,117,867 B2 | 10/2006 | Cox et al. |
| 7,832,410 B2 | 11/2010 | Hon |
| 8,314,591 B2 | 11/2012 | Terry et al. |
| 8,365,742 B2 | 2/2013 | Hon |
| 8,499,766 B1 | 8/2013 | Newton |
| 9,179,707 B2 | 11/2015 | Kaljura et al. |
| 2005/0016550 A1 | 1/2005 | Katase |
| 2006/0196518 A1 | 9/2006 | Hon |
| 2007/0186943 A1 | 8/2007 | Strickland et al. |
| 2008/0092912 A1 | 4/2008 | Robinson et al. |
| 2009/0095311 A1 | 4/2009 | Hon |
| 2009/0126745 A1 | 5/2009 | Hon |
| 2009/0188490 A1 | 7/2009 | Hon |
| 2009/0272379 A1 | 11/2009 | Thorens et al. |
| 2011/0094523 A1 | 4/2011 | Thorens et al. |
| 2011/0126848 A1 | 6/2011 | Zuber et al. |
| 2011/0139669 A1 | 6/2011 | Huppert et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0290248 A1 | 12/2011 | Schennum |
| 2012/0111347 A1 | 5/2012 | Hon |
| 2012/0260927 A1 | 10/2012 | Liu |
| 2012/0279512 A1 | 11/2012 | Hon |
| 2013/0037041 A1 | 2/2013 | Worm et al. |
| 2013/0056013 A1 | 3/2013 | Terry et al. |
| 2013/0306084 A1 | 11/2013 | Flick |
| 2014/0000638 A1 | 1/2014 | Sebastian et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0166029 A1 | 6/2014 | Weigensberg et al. |
| 2014/0209105 A1 | 7/2014 | Sears et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2016/0120224 A1 | 5/2016 | Mishra |
| 2016/0338402 A1* | 11/2016 | Buehler ............... B23K 26/362 |
| 2017/0027218 A1 | 2/2017 | Tilburg et al. |
| 2017/0064995 A1 | 3/2017 | Beeson |
| 2017/0164657 A1 | 6/2017 | Batista |
| 2018/0271140 A1 | 9/2018 | Kobal et al. |
| 2019/0200673 A1 | 7/2019 | Bless |
| 2019/0289909 A1 | 9/2019 | Hejazi |
| 2020/0352256 A1 | 11/2020 | Hejazi et al. |
| 2021/0212364 A1* | 7/2021 | Batista ................. A24B 15/165 |
| 2021/0368860 A1* | 12/2021 | Reevell ................. A24B 15/281 |
| 2023/0189877 A1* | 6/2023 | Crump .................... A24B 15/42 |
| | | 131/329 |
| 2023/0320420 A1* | 10/2023 | Rogan .................... A24F 40/485 |
| | | 131/329 |

FOREIGN PATENT DOCUMENTS

| | | |
|---|---|---|
| CN | 201379072 | 1/2010 |
| EA | 15556 B1 | 6/2007 |
| EA | 200800605 A1 | 6/2008 |
| EP | 0 295 122 | 12/1988 |
| EP | 0 845 220 | 6/1998 |
| EP | 1 618 803 | 1/2006 |
| EP | 175419 A1 | 2/2007 |
| GB | 2469850 | 11/2010 |
| RU | 2614617 C2 | 3/2017 |
| WO | WO 2003/034847 | 5/2003 |
| WO | WO 2004/080216 | 9/2004 |
| WO | WO 2005/099494 | 10/2005 |
| WO | WO 2007/131449 | 11/2007 |
| WO | WO 2015/128028 A1 | 9/2015 |
| WO | WO 2020/229961 | 11/2020 |

OTHER PUBLICATIONS

RU Office Action dated Apr. 19, 2024 of related RU Patent Application No. 2022115214, filed Dec. 9, 2020.

* cited by examiner

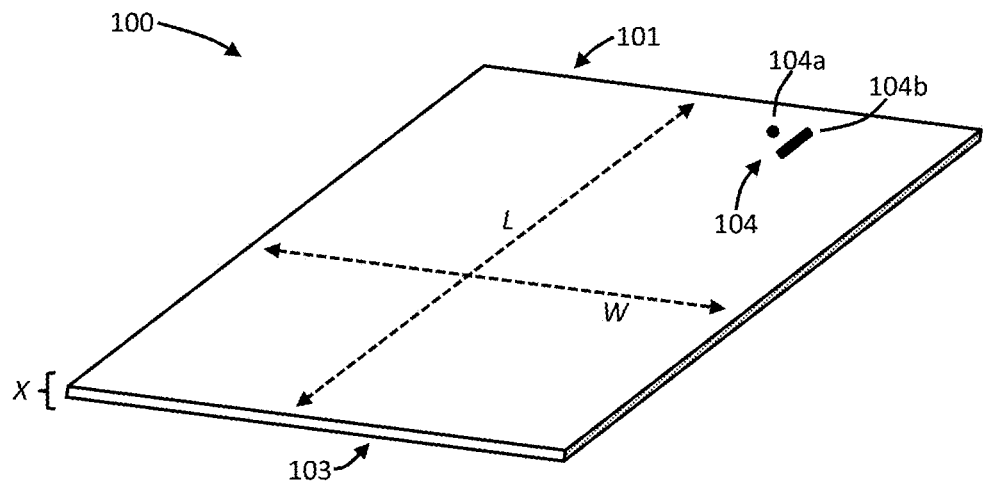
FIG. 2A
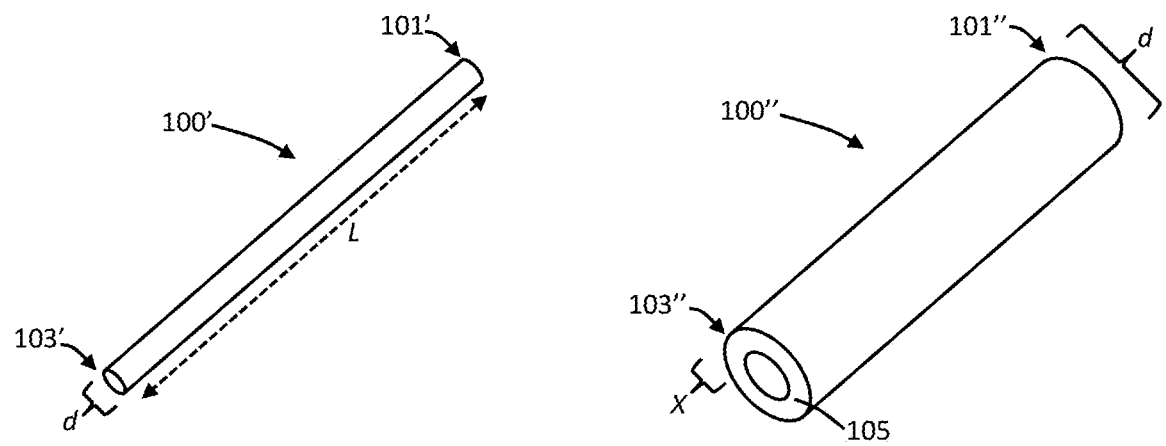
FIG. 2B
FIG. 2C

AEROSOL DELIVERY DEVICE WITH DOWNSTREAM FLAVOR CARTRIDGE

CROSS-REFERENCE TO RELATED APPLICATIONS

The present application is a continuation of U.S. patent application Ser. No. 16/708,785, filed Dec. 10, 2019, which is incorporated by reference herein in its entirety.

FIELD OF THE DISCLOSURE

The present disclosure relates to flavor delivery devices configured for combination with aerosol delivery devices. More particularly, such flavor delivery device can comprise an elongated flavor substrate including at least one flavor material, the flavor substrate being substantially surrounded by an outer sleeve and optionally positioned substantially within an outer frame.

BACKGROUND

Many smoking articles have been proposed through the years as improvements upon, or alternatives to, smoking products based upon combusting tobacco. Example alternatives have included devices wherein a solid or liquid fuel is combusted to transfer heat to tobacco or wherein a chemical reaction is used to provide such heat source. Examples include the smoking articles described in U.S. Pat. No. 9,078,473 to Worm et al., which is incorporated herein by reference.

The goal of the improvements or alternatives to smoking articles typically has been to provide the sensations associated with cigarette, cigar, or pipe smoking, without delivering considerable quantities of incomplete combustion and pyrolysis products. To this end, there have been proposed numerous smoking products, flavor generators, and medicinal inhalers which utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al.; and U.S. Pat. App. Pub. Nos. 2013/0255702 to Griffith, Jr. et al.; and 2014/0096781 to Sears et al., which are incorporated herein by reference. See also, for example, the various types of smoking articles, aerosol delivery devices and electrically powered heat generating sources referenced by brand name and commercial source in U.S. Pat. App. Pub. No. 2015/0220232 to Bless et al., which is incorporated herein by reference. Additional types of smoking articles, aerosol delivery devices and electrically powered heat generating sources referenced by brand name and commercial source are listed in U.S. Pat. App. Pub. No. 2015/0245659 to DePiano et al., which is also incorporated herein by reference in its entirety. Other representative cigarettes or smoking articles that have been described and, in some instances, been made commercially available include those described in U.S. Pat. No. 4,735,217 to Gerth et al.; U.S. Pat. Nos. 4,922,901, 4,947,874, and 4,947,875 to Brooks et al.; U.S. Pat. No. 5,060,671 to Counts et al.; U.S. Pat. No. 5,249,586 to Morgan et al.; U.S. Pat. No. 5,388,594 to Counts et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,726,320 to Robinson et al.; U.S. Pat. No. 7,896,006 to Hamano; U.S. Pat. No. 6,772,756 to Shayan; U.S. Pat. App. Pub. No. 2009/0095311 to Hon; U.S. Pat. App. Pub. Nos. 2006/0196518, 2009/0126745, and 2009/0188490 to Hon; U.S. Pat. App. Pub. No. 2009/0272379 to Thorens et al.; U.S. Pat. App. Pub. Nos. 2009/0260641 and 2009/0260642 to Monsees et al.; U.S. Pat. App. Pub. Nos. 2008/0149118 and 2010/0024834 to Oglesby et al.; U.S. Pat. App. Pub. No. 2010/0307518 to Wang; and WO 2010/091593 to Hon, which are incorporated herein by reference.

Representative products that resemble many of the attributes of traditional types of cigarettes, cigars or pipes have been marketed as ACCORD® by Philip Morris Incorporated; ALPHA™, JOYE 510™ and M4™ by InnoVapor LLC; CIRRUS™ and FLING™ by White Cloud Cigarettes; BLU™ by Lorillard Technologies, Inc.; COHITA™, COLIBRI™, ELITE CLASSIC™, MAGNUM™, PHANTOM™ and SENSE™ by EPUFFER® International Inc.; DUOPRO™, STORM™ and VAPORKING® by Electronic Cigarettes, Inc.; EGAR™ by Egar Australia; eGo-C™ and eGo-T™ by Joyetech; ELUSION™ by Elusion UK Ltd; EONSMOKE® by Eonsmoke LLC; FIN™ by FIN Branding Group, LLC; SMOKE® by Green Smoke Inc. USA; GREENARETTE™ by Greenarette LLC; HALLIGAN™ HENDU™ JET™, MAXXQ™ PINK™ and PITBULL™ by SMOKE STIK®; HEATBAR™ by Philip Morris International, Inc.; HYDRO IMPERIAL™ and LXE™ from Crown7; LOGIC™ and THE CUBAN™ by LOGIC Technology; LUCI by Luciano Smokes Inc.; METRO® by Nicotek, LLC; NJOY® and ONEJOY™ by Sottera, Inc.; NO. 7™ by SS Choice LLC; PREMIUM ELECTRONIC CIGARETTE™ by PremiumEstore LLC; RAPP E-MYSTICK™ by Ruyan America, Inc.; RED DRAGON™ by Red Dragon Products, LLC; RUYAN® by Ruyan Group (Holdings) Ltd.; SF® by Smoker Friendly International, LLC; GREEN SMART SMOKER® by The Smart Smoking Electronic Cigarette Company Ltd.; SMOKE ASSIST® by Coastline Products LLC; SMOKING EVERYWHERE® by Smoking Everywhere, Inc.; V2CIGS™ by VMR Products LLC; VAPOR NINE™ by VaporNine LLC; VAPOR4LIFE® by Vapor 4 Life, Inc.; VEPPO™ by E-CigaretteDirect, LLC; VUSE® by R. J. Reynolds Vapor Company; Mistic Menthol product by Mistic Ecigs; and the Vype product by CN Creative Ltd. Yet other electrically powered aerosol delivery devices, and in particular those devices that have been characterized as so-called electronic cigarettes, have been marketed under the tradenames COOLER VISIONS™; DIRECT E-CIG™; DRAGONFLY™; EMIST™; EVERSMOKE™; GAMUCCI®; HYBRID FLAME™; KNIGHT STICKS™; ROYAL BLUES™; SMOKETIP®; SOUTH BEACH SMOKE™.

There remains a need in the art for further means for adding flavoring to aerosols. Accordingly, it would be desirable to provide a flavor delivery device configurable for easy combination with an aerosol delivery device to add a flavor or a mixture of flavors to a formed aerosol as desired by the user.

BRIEF SUMMARY OF INVENTION

In various embodiments, the present disclosure provides a flavor delivery device that can be included in, or combined with, an aerosol delivery device. The flavor delivery device can incorporate at least one elongated flavor substrate that is adapted to or configured to retain a flavor material that may be released therefrom for entrainment in an aerosol stream. As such, the flavor delivery device is configured for inclusion within or attachment to an aerosol delivery device whereas the flavor delivery device is located downstream of a liquid reservoir in the aerosol delivery device which contains, for example, an e-liquid. The flavor delivery device containing a different flavor material can either boost the flavor from the e-liquid or generate a flavor when an unflavored e-liquid is used.

In one aspect of the disclosure, the flavor delivery device includes at least one elongated flavor substrate which is made out of a porous material. The elongated flavor substrate extends along a longitudinal axis between two ends where the first end opposes the second end.

The elongated flavor substrate includes flavor material.

The flavor delivery device also includes an outer sleeve which surrounds the perimeter of the at least one elongated flavor substrate. The outer sleeve is impermeable to the flavor material. In some embodiments, the flavor delivery device can be further characterized in relation to one or more of the following statements, which can be combined in any number or order.

One or more of the following conditions can be met: the at least one elongated flavor substrate can be in the form of one or more rods; the at least one elongated flavor substrate can be in the form of one or more tubes; the at least one elongated flavor substrate can be in the form of one of a pleated sheet; the at least one elongated flavor substrate can be in the form of a gathered sheet; the at least one elongated flavor substrate can be in the form of a rolled sheet.

The porous material forming the at least one elongated flavor substrate can be a polymeric material.

The polymeric material forming the at least one elongated flavor substrate can be selected from a group consisting of: polyethylene, polypropylene, polyether, polyester, polylactic acid (PLA), cellulose acetate, nylon, ceramics, or any combination thereof.

The material forming the outer sleeve that surrounds the at least one elongated flavor substrate can be selected from a group consisting of silicone, polyether, polyester, polypropylene, polylactic acid (PLA), nylon, or any combination thereof.

The at least one elongated flavor substrate can be formed by multiple layers.

Each layer further can comprise material with different densities.

Each layer can be configured to release the flavor material at a different rate.

Each layer further can comprise different flavor material.

The flavor delivery device can further comprise the at least one elongated substrate which is made out of multiple fibers.

The multiple fibers may be sheath core fibers.

The sheath can be a porous material where the core includes flavor material.

The flavor delivery device can further comprise an outer shell which extends along a longitudinal axis between a distal end including at least one opening and a proximal end including at least one opening. The outer shell defines a chamber where the at least one elongated flavor substrate is positioned within the chamber of the outer shell such that the longitudinal axis of the at least one elongated substrate is substantially parallel with the longitudinal axis of the outer shell.

The outer housing of the flavor delivery device can comprise one or more openings formed within the outer wall of the housing.

The elongated flavored delivery device can be removable and replaceable.

The proximate end of the outer shell of the flavor delivery device can be configured for engagement with a mouthend of a smoking device.

In another embodiment of the present disclosure, at least a portion of the flavor material can be provided within a breakable capsule.

The flavored delivery device can include multiple breakable capsules.

The breakable capsules can include capsules of at least two significantly different sizes.

In another aspect of the disclosure, a cartridge for an aerosol delivery device is provided. The cartridge can comprise, for example, a cartridge housing having a mouthend; a reservoir which includes an aerosol precursor composition; a heater adapted to vaporize the aerosol precursor composition; and a flavored delivery device as otherwise described herein which is located downstream from the reservoir relative to the mouthend of the cartridge.

BRIEF DESCRIPTION OF THE DRAWINGS

In order to assist the understanding of aspects of the disclosure, reference will now be made to the appended drawings, which are not necessarily drawn to scale and in which like reference numerals refer to like elements. The drawings are provided by way of example only, and should not be construed as limiting the disclosure.

FIG. 2A is a perspective view of an example embodiment of a flavor substrate configure in a substantially sheet-like form according to the present disclosure;

FIG. 2B is a perspective view of an example embodiment of a flavor substrate configured in a substantially rod-like form according to the present disclosure;

FIG. 2C is a perspective view of an example embodiment of a flavor substrate configured in a substantially tube-like form according to the present disclosure;

DETAILED DESCRIPTION

Figure 1A:
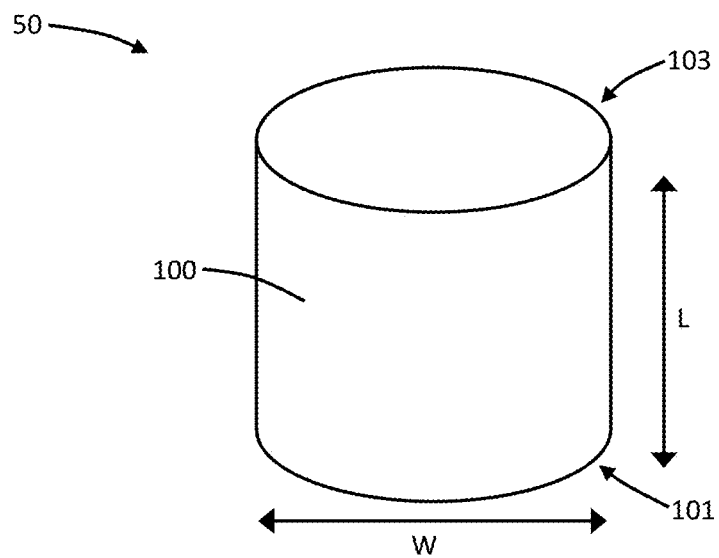
FIG. 1A is a front view of an example flavor delivery device.

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural variations unless the context clearly dictates otherwise.

The present disclosure provides descriptions of flavor delivery devices that are adapted to or configured to provide a flavor to a passing vapor or aerosol stream. The flavor delivery device is particularly suited for combination with aerosol delivery devices. As such, the flavor delivery device is adapted to or configured to add flavor to an aerosol that is formed in the aerosol delivery device. The aerosol delivery devices may use electrical energy to heat a material to form an inhalable substance; such articles may be sufficiently compact to be considered "hand-held" devices. An aerosol delivery device may provide some or all of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe, without any substantial degree of combustion of any component of that article or device. The aerosol delivery devices may not produce smoke in the sense of the aerosol resulting from by-products of combustion or pyrolysis of tobacco, but rather, that the article or device may yield vapors (including vapors within aerosols that can be considered to be visible aerosols that might be considered to be described as smoke-like) resulting from volatilization or vaporization of certain components of the article or device, although in other implementations the aerosol may not be visible. In some implementations, aerosol delivery devices may incorporate tobacco and/or components derived from tobacco. As such, the aerosol delivery devices can be characterized as an electronic smoking article such as an electronic cigarette or "e-cigarette."

While the flavor delivery device is generally described herein in terms of implementations associated with aerosol delivery devices such as so-called "e-cigarettes," it should be understood that the mechanisms, components, features, and methods may be embodied in many different forms and associated with a variety of articles. For example, the description provided herein may be employed in conjunction with implementations of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of embodiments relating to aerosol delivery devices by way of example only, and may be embodied and used in various other products and methods.

Aerosol delivery devices incorporating a flavor delivery device according to the present disclosure also can be characterized as being vapor-producing articles or medicament delivery devices. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, aerosol delivery devices incorporating a flavor delivery device of the present disclosure may be subjected to many of the physical actions employed by an individual in using a traditional type of smoking article (e.g., a cigarette, cigar or pipe that is employed by lighting and inhaling tobacco). For example, the user of a device of the present disclosure can hold that article much like a traditional type of smoking article, draw on one end of that article for inhalation of aerosol produced by that article, take puffs at selected intervals of time, etc.

In one or more embodiments, the present disclosure thus can provide a flavor delivery device, which can include at least a flavor substrate. The flavor material may be, for example, adsorbed and/or absorbed by the flavor substrate. In particular, the flavor material may be at least partially retained within pores of the flavor substrate. The retaining of the flavor material by the flavor substrate is preferably a releasable relationship so that the flavor material may be released from the flavor substrate to be entrained into a passing aerosol stream. As will be further evident from the description provided herein, the flavor delivery article may further include a flavor material that is combinable with the flavor substrate so as to be retained thereby. Moreover, the flavor substrate alone or already in combination with the flavor material may be combined with a sheath and/or an outer housing. Further, the flavor substrate may include one or more capsules combinable therewith.

Figure 1B:
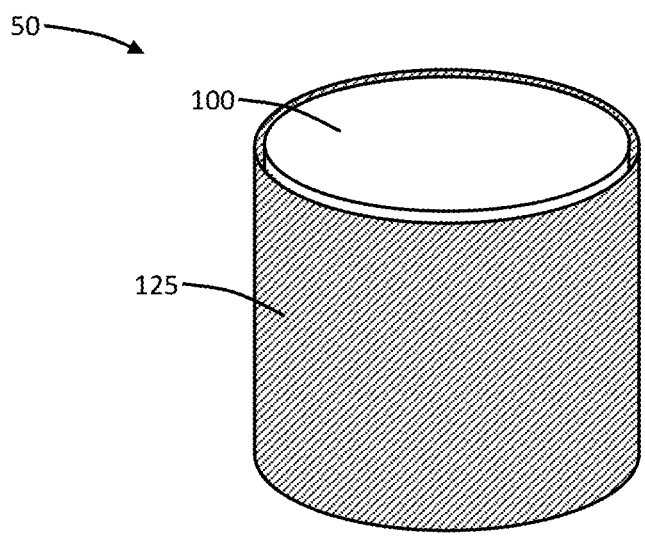
FIG. 1B is a front view of an example flavor delivery device surrounded by an optional outer sleeve.

An example embodiment of a flavor delivery device 50 is shown in FIGS. 1A and 1B. As seen therein in FIG. 1A, the flavor delivery device 50 can comprise at least one elongated flavor substrate 100 that is preferably formed of a porous material such that the flavor substrate can be adapted to or configured to retain and release a flavor material. FIG. 1B shows the at least one elongated flavor substrate 100 where the outer perimeter is surrounded by an optional outer sleeve 125. Preferably, the outer sleeve 125 can be substantially impermeable to the flavor material retained by the flavor substrate 100. As illustrated, the flavor substrate is substantially in the form of a cylinder; however, it is understood that other configurations are also encompassed by the present disclosure, as will be more apparent from the further example embodiments provided herein. The outer sleeve 125 can be present around at least a portion of an outer surface of the flavor substrate 100 and thus may surround at least a portion or substantially all of the outer perimeter of the substrate. Preferably, the flavor sleeve 125 is not present at the opposing ends (101, 103) of the flavor substrate 100 so that an aerosol may pass from one end to the other end so as to entrain flavor material while passing through the flavor substrate.

In some embodiments, the illustrated flavor substrate 100 is configured to extend along a longitudinal axis between a first end 101 and an opposing second end 103 and, as such, can have at least a longitudinal dimension or a length L. The flavor substrate 100 can vary in shape, as further discussed below, and thus can include further dimensions, such as thickness and/or width W. For example, the flavor substrate 100 can be configured so that a substantially large surface area is provided for passage of flavor liquid from the flavor substrate to an aerosol stream passing along and/or through the flavor substrate. This can be achieved by providing the flavor substrate in a specified configuration and/or by providing a plurality of flavor substrates in combination. Such options are evident in relation to the example embodiments illustrated in FIG. 2A through FIG. 2C. As seen in FIG. 2A, the flavor substrate 100 extends along a longitudinal axis L between a first end 101 and a second end 103 and has a width W that extends along an axis that is perpendicular to the longitudinal axis L and a thickness X As such, the flavor substrate 100 can be substantially in the form of a sheet having a length (L) of about 0.2 cm to about 5 cm, about 0.3 cm to about 3 cm, about 0.4 cm to about 2.5 cm, or about 0.5 cm to about 2 cm. The flavor substrate likewise can have a width (W) of about 10% of the length to about 4000% of the length, about 20% of the length to about 2000% of the length, or about 50% of the length to about 1000% of the length. The thickness (X) can be about 5 microns to about 500 microns, about 10 microns to about 400 microns, or about 20 microns to about 300 microns. A flavor substrate 100 substantially in the form of a sheet can thus be adapted to or configured to be substantially flat. If desired, a flavor substrate 100 formed as a flat sheet can be embossed and/or include a plurality of perforations 104 therethrough. Perforations may be substantially round (see perforation 104*a* or may be elongated (e.g., in the form of slits)—see perforation 104*b*).

As seen in FIG. 2B, the flavor substrate 100' again extends along a longitudinal axis L between a first end 101' and a second end 103' and is substantially in the form of a rod having a diameter d. The flavor substrate 101' in the form of a rod can have a length (L) of about 0.2 cm to about 5 cm, about 0.3 cm to about 3 cm, about 0.4 cm to about 2.5 cm, or about 0.5 cm to about 2 cm and can have a diameter of about 1 micron to about 2,000 microns, about 5 microns to about 1,500 microns, or about 10 microns to about 1,000 microns.

As seen in FIG. 2C, the flavor substrate 100" again extends along a longitudinal axis L between a first end 101" and a second end 103" and is substantially in the form of a hollow tube having a diameter d. The flavor substrate 101" in the form of a tube can have a length (L) of about 0.2 cm to about 5 cm, about 0.3 cm to about 3 cm, about 0.4 cm to about 2.5 cm, or about 0.5 cm to about 2 cm and can have a diameter of about 0.5 mm to about 25 mm, about 1 mm to about 20 mm, or about 2 mm to about 15 mm. The tube can have a substantially continuous wall 105 that can vary in thickness X along the longitudinal axis of the flavor substrate 100". In some embodiments, the thickness X of the substantially continuous wall 105 is preferably substantially uniform along the longitudinal axis of the flavor substrate 100". The substantially continuous wall 105, for example, can have an average thickness X of about 0.01 mm to about 5 mm, about 0.1 mm to about 4 mm, or about 0.2 mm to about 2 mm. Wall thickness may be substantially uniform (e.g., varying by no more than about 15%, no more than about 10%, no more than about 5%, or no more than about 2% along substantially the entire length of the tube. In some embodiments, wall thickness may vary along the length of the tube.

The flavor substrate in the form of a tube or rod may take on a variety of shapes and may have, for example, a cross-sectional shape, such as a circle, square, rectangle, oval, triangle, polygon, or the like. Although illustrated as having a substantially continuous diameter or thickness, in some embodiments, the diameter and/or thickness of the flavor substrate (or a wall of the flavor substrate) can vary along the length thereof. For example, the diameter and/or thickness may increase from the first end (101, 101', 101") to the second end (103, 103', 103") so that a diameter and/or thickness of the second end is greater than a diameter and/or thickness of the first end by about 1% to about 600%, about 25% to about 500%, about 50% to about 400%, or about 75% to about 250%. Alternatively, the diameter and/or thickness may decrease from the first end (101, 101', 101") to the second end (103, 103', 103") so that a diameter and/or thickness of the second end is greater than the diameter of the first end by about 1% to about 600%, about 25% to about 500%, about 50% to about 400%, or about 75% to about 250%.

Figure 3A:
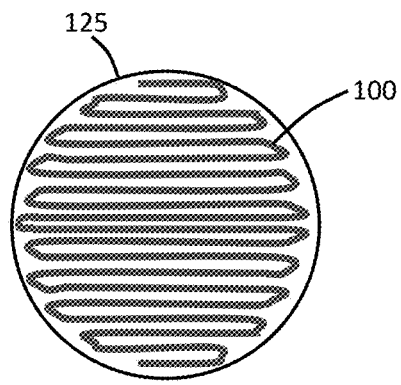
FIG. 3A is a partial cross-sectional view of an example embodiment of flavor substrate that is at least partially circumscribed by an outer film, wherein the flavor substrate is configured as a pleated sheet.
Figure 3B:
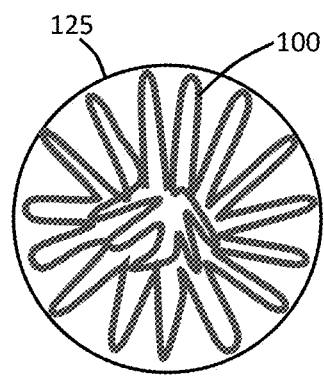
FIG. 3B is a partial cross-sectional view of an example embodiment of flavor substrate that is at least partially circumscribed by an outer film, wherein the flavor substrate is configured as a gathered sheet.
Figure 3C:
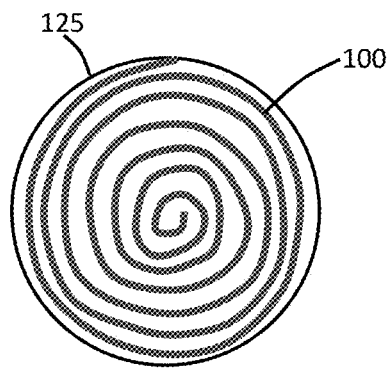
FIG. 3C is a partial cross-sectional view of an example embodiment of flavor substrate that is at least partially circumscribed by an outer film, wherein the flavor substrate is configured as a rolled sheet.

The flavor substrate (100, 100', 100") can be configured so that a substantially large surface area is provided for passage of flavor liquid from the flavor substrate to an aerosol stream passing along the longitudinal length of the flavor substrate. This can be achieved by providing the flavor substrate in a specified configuration and/or by providing a plurality of flavor substrates in combination. FIG. 3A, for example illustrates a flavor substrate 100 that is in a folded or pleated configuration. An optional, outer sleeve 125 is also shown. As a further example, FIG. 3B illustrates a flavor substrate 100 that is in a gathered configuration and surrounded by an optional outer sleeve 125. As another example, FIG. 3C illustrates a flavor substrate 100 that is in a rolled configuration and surrounded by an optional outer sleeve 125. A flavor substrate 100 substantially in the form of a sheet can be provided in any one or more of the foregoing configuration as well as further, similar configurations wherein the sheet is aggregated in a manner to maximize the available surface area across which an aerosol or similar fluid may flow. Although only a single sheet is illustrated as being aggregated (e.g., folded, gathered, or rolled), it is understood that a plurality of sheets (e.g., two, three, four, five, or even more) may be combined. Moreover, when a plurality of sheets is used, two or more individual sheets may be formed of different materials and/or be adapted to or configured to provide different properties. For example, two sheets (or more sheets) adapted to provide two or more different flavors may be utilized to provide a desired flavor combination.

Figure 3D:
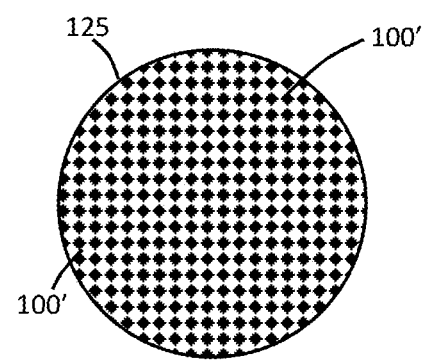
FIG. 3D is a partial cross-sectional view of an example embodiment of flavor substrate that is at least partially circumscribed by an outer film, wherein the flavor substrate is configured as a plurality of rods.
Figure 3E:
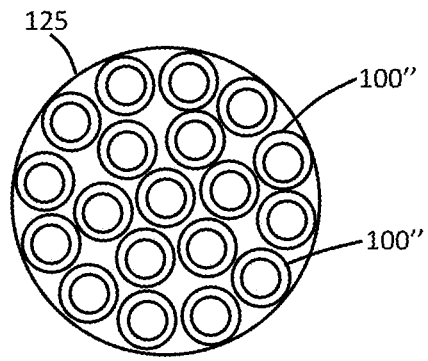
FIG. 3E is a partial cross-sectional view of an example embodiment of flavor substrate that is at least partially circumscribed by an outer film, wherein the flavor substrate is configured as a plurality of tubes.
Figure 3F:
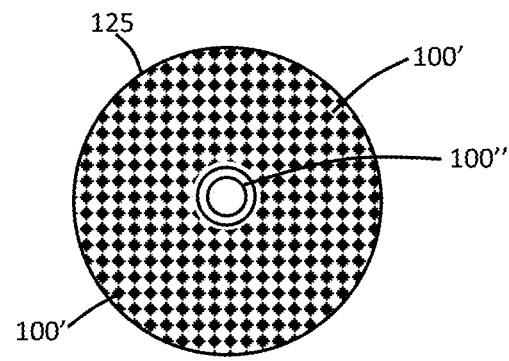
FIG. 3F is a partial cross-sectional view of an example embodiment of flavor substrate that is at least partially circumscribed by an outer film, wherein the flavor substrate is configured as a combination of a tube and a plurality of rods.
Figure 3G:
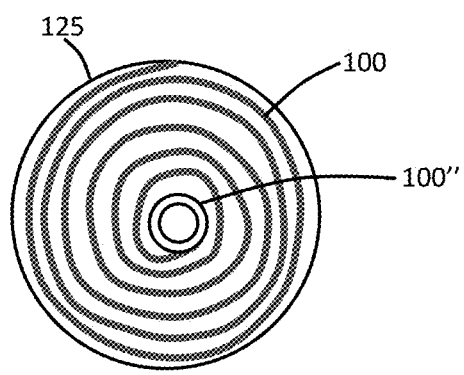
FIG. 3G is a partial cross-sectional view of an example embodiment of flavor substrate that is at least partially circumscribed by an outer film, wherein the flavor substrate is configured as a combination of a rolled sheet and a plurality of tubes.

As yet a further example, FIG. 3D illustrates a plurality of flavor substrates 100' that are provided in the form of rods having a substantially square cross-section (although any shaped cross-section is envisioned) and being surrounded by an optional outer sleeve 125. The plurality of rods is shown in a grid-like pattern, but any packing style may be utilized. As still another example, FIG. 3E illustrates a plurality of flavor substrates 100" that are provided in the form of tubes having a substantially round cross-section (although any shaped cross-section is envisioned) and being surrounded by an optional outer sleeve 125. The plurality of tubes may be provided with any packing style desired. As yet another example, FIG. 3F illustrates the use of two different types of flavor substrates. A plurality of flavor substrates 100' in the form of rods are included along with a single flavor substrate 100" in the form of a tube, all being surrounded by an optional outer sleeve 125. Again, the rods and tubes may have any desired cross-section and may be provided in any desired number. In particular, although only a single flavor substrate tube 100" is illustrated, it is understood that a plurality of flavor substrate rods 100' may be combined with a plurality of flavor substrate tubes 100". As yet a further example, FIG. 3G also illustrates the use of two different types of flavor substrates. A flavor substrate 100 in the form of a sheet is included with a single flavor substrate 100" in the form of a tube, all being surrounded by an optional outer sleeve 125. Again, the sheet and tube may have any desired cross-section and may be provided in any desired number (e.g., a single sheet with a plurality of tubes, a single tube with a plurality of sheets, or a plurality of sheets with a plurality of tubes). Likewise, any number of flavor substrate rod(s) 100' and/or flavor substrate tube(s) 100" may be combined with any number of flavor substrate sheet(s) 100 that may be pleated, gathered, or wrapped.

In some embodiments, the porous material forming the flavor substrate (100, 100', 100") may be formed at least in part from one or more polymeric materials, such as polyethersulfone, polypropylene, polyethylene, polyester (e.g., polyethylene terephthalate and polypropylene terephthalate), nylon, polylactic acid (PLA), cellulosic materials (e.g., cellulose nitrate, regenerated cellulose, cellulose acetate), silica, cotton, ceramics, and combinations thereof. Biodegradable polymers likewise may be utilized for this purpose. For example, the flavor substrate (100, 100', 100") may be formed at least partially from fibers formed from any of the foregoing materials alone or in one or more combinations. Likewise, any one or more of the foregoing materials may be expressly excluded from use in one or more embodiments of the disclosure.

In further embodiments, the elongated flavor substrate 100 in the flavor delivery device 50 can be formed by one or more layers. A greater number of layers may be utilized, and each layer may be formed by the same or different material. Further, individual layers may be adapted or configured to exhibit specific properties that can be independent from the remaining layer(s). Each layer can independent exhibit the same or different densities, porosities, thicknesses, materials, or other properties and/or structural features. The elongated flavor substrate 100 may be formed by one layer, two layers, three layers, four layers, or more layers. When more than one layer is used, the layers can be prepared using coextrusion or other known techniques in the art. In some embodiments, use of materials having one or more different properties as noted above in forming individual layers can be effective to provide desired outcomes, such as providing differing release rates of the flavor material. For example, a different release rate among the layers may be desired in order to create a different flavor profile, different from each individual layer. More particularly, a layer whose composition includes materials of higher density can be effective to provide for a relatively slower release of flavor material entrained therein, whereas a layer composed of lower density materials would can be effective to provide for a relatively faster release of flavor material entrained therein.

In one or more embodiments, a flavor substrate 100 according to the present disclosure can comprise or can be substantially formed from a plurality of fibers. The term "fiber" as used herein includes both fibers of finite length, such as conventional staple fibers and nanofibers, as well as substantially continuous structures, such as continuous filaments, unless otherwise indicated. The fibers can have a substantially round or circular cross section or non-circular cross sections (for example, oval, rectangular, multi-lobed, and the like). The fibers can be provided in a variety of configurations, and the fibers particularly can include multicomponent fibers. As used herein, the term "multicomponent fibers" includes staple and continuous fibers prepared from two or more polymers present in discrete structured domains in the fiber, as opposed to blends where the domains tend to be dispersed, random or unstructured. For purposes of illustration only, the present subject matter is generally described in terms of an example bicomponent fiber comprising two polymer components; however, the present disclosure further expressly includes fibers with two or more structured components and is not limited to the example bicomponent fibers described below. Although the disclosed embodiments are not limited to two components, the terms first component and second component are used throughout for the ease of description.

Multicomponent fibers may comprise a plurality of polymer components that can be arranged in substantially constantly positioned distinct zones across the cross section of the multicomponent fiber and extend continuously along the length of the multicomponent fiber. Both the shape of the fiber and the configuration of the components therein will depend upon the equipment that is used in the preparation of the fiber, the process conditions, and the melt viscosities of the various components. A wide variety of fiber configurations are possible, but the cross section of the multicomponent fiber can particularly be circular, since the equipment typically used in the production of multicomponent synthetic fibers often produces fibers with a substantially circular cross section; however, other cross sections are encompassed.

Figure 4A:
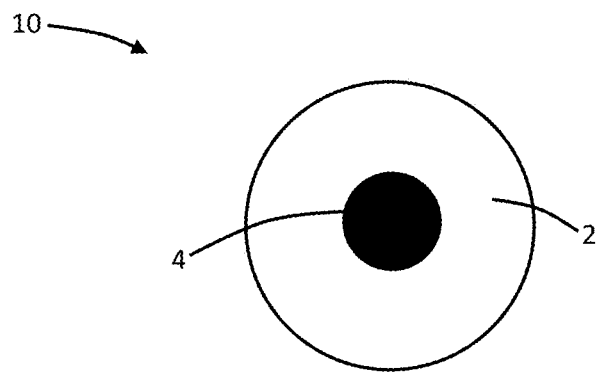
FIG. 4A is a transverse cross sectional view of an example sheath/core multicomponent fiber.
Figure 4B:
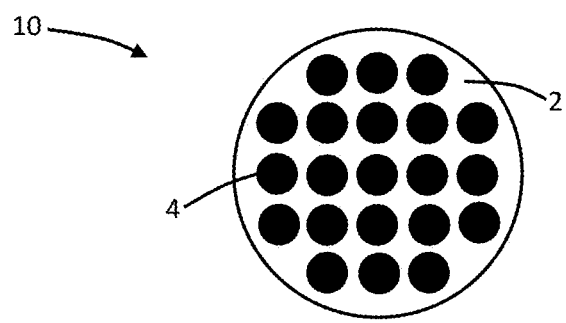
FIG. 4B is a transverse cross sectional view of an example "islands in the sea" multicomponent fiber.

Non-limiting examples of multicomponent fibers that may be used in flavor substrate according to the present disclosure are illustrated in FIG. 4A and FIG. 4B. FIG. 4A provides a cross-sectional view of an example multicomponent fiber 10 in the form of a sheath/core fiber that includes at least two structured polymer components: (i) an outer sheath component 2 comprising a first polymer; and (ii) an inner core component 4 comprising a second polymer. The core component 4 may be substantially centrally positioned within the outer sheath component 2 in a substantially concentric configuration, as illustrated, or may be off-centered in a substantially eccentric configuration. FIG. 4B illustrates a further example embodiment of a multicomponent fiber 10 configured as a "matrix" or "islands in a sea" type fiber having a plurality of inner, or "island," polymer components surrounded by an outer matrix, or "sea," polymer component. The island components 4 can be substantially uniformly arranged within the matrix or the sea component 2, such as illustrated in FIG. 4B. Alternatively, the island components 4' can be randomly distributed within the sea component 2. In various embodiments, the sea polymer component 2 can comprise the first polymer component, and island polymer components 4 can comprise the second polymer component.

Methods for making multicomponent fibers are well known and need not be described here in detail. Generally, to form a multicomponent fiber, at least two polymers are extruded separately and fed into a polymer distribution system wherein the polymers are introduced into a segmented spinneret plate. The polymers follow separate paths to the fiber spinneret and are combined in a spinneret hole. The spinneret is configured so that the extrudant has the desired shape.

Following extrusion through the die, the resulting thin fluid strands, or filaments, remain in the molten state for some distance before they are solidified by cooling in a surrounding fluid medium, which may be chilled air blown through the strands. Once solidified, the filaments are taken up on a godet or another take-up surface. In a continuous filament process, the strands are taken up on a godet which draws down the thin fluid streams in proportion to the speed of the take-up godet. In the jet process, the strands are collected in a jet, such as for example, an air gun, and blown onto a take-up surface such as a roller or a moving belt to form a spunbond web. In the meltblown process, air is ejected at the surface of the spinneret which serves to simultaneously draw down and cool the thin fluid streams as they are deposited on a take-up surface in the path of cooling air, thereby forming a fiber web. Regardless of the type of melt spinning procedure which is used, it is important that the thin fluid streams be melt drawn down in a molten state, i.e. before solidification occurs, to reduce the diameter of the fibers. Typical melt draw down ratios known in the art may be utilized. Where a continuous filament or staple process is employed, it may be desirable to draw the strands in the solid state with conventional drawing equipment, such as, for example, sequential godets operating at differential speeds. See, for example, U.S. Pat. No. 5,082,899, incorporated herein by reference in its entirety.

Following drawing in the solid state, the continuous filaments may be crimped or texturized and cut into a desirable fiber length, thereby producing staple fiber. The length of the staple fibers generally ranges from about 25 to about 50 millimeters, although the fibers can be longer or shorter as desired. See, for example, U.S. Pat. No. 4,789,592 to Taniguchi et al. and U.S. Pat. No. 5,336,552 to Strack et al., each of which is herein incorporated by reference in its entirety.

The multicomponent fibers of the various embodiments can be staple fibers, tows, spunbond filaments, continuous filaments, or meltblown fibers. In general, staple, multifilament, and spunbond fibers formed in accordance with the present embodiment can have a fineness of about 0.5 to about 100 denier. Meltblown filaments can have a fineness of about 0.001 to about 10.0 denier. Monofilament fibers can have a fineness of about 50 to about 10,000 denier.

The multicomponent fibers can be incorporated into or formed into a flavor substrate as otherwise described herein. The fibers, for example, may be formed into nonwoven webs by any means suitable in the art, particularly wherein heat bonding is used. In addition, continuous filament may be spun directly into nonwoven webs by a spunbonding process. Fibers other than the multicomponent fibers discussed above may be present as well, including any of the various synthetic and/or natural fibers known in the art or otherwise listed in the present disclosure. Example synthetic fibers include polyolefin, polyester, polyamide, acrylic, rayon, cellulose acetate, thermoplastic multicomponent fibers (such as conventional sheath/core fibers, for example polyethylene sheath/polyester core fibers) and the like and mixtures thereof. Example natural fibers include wool, cotton, wood pulp fibers and the like and mixtures thereof.

The first polymer component and the second polymer component can be formed from any material as otherwise described herein. In some embodiments, the first polymer component (e.g., forming the sheath or sea component of the multicomponent fibers) can be adapted or configured to be substantially porous. Non-limiting examples of polymers that can be used in making a porous sheath include nylon, polyethylene, polypropylene, polyester, polyimide, polyether ether ketone (PEEK), polyurethane, polytetrafluoroethylene, and Pebax®. Preparing these porous materials can be done by known methods described in the art such as electrospinning. The second polymer component (e.g., forming the core or islands component of the multicomponent fibers) can be adapted or configured for having a flavor material as described herein combined therewith and then releasing the flavor material through the first polymer component. The sheath or sea component may thus be adapted or configured to preserve the flavor material(s) mixed with the second polymer component for an extended period of time which extends the flavor delivery. In other words, extend flavor delivery or controlled flavor delivery may be achieved so that the flavor material added to a passing aerosol stream is substantially continuous over time instead of experiencing a reduction in flavor transfer over time.

In one or more embodiments, the flavor substrate 100 can be prepared, at least in part, from a tobacco material, including but not limited to reconstituted tobacco. Suitable reconstituted tobacco can be that prepared utilizing any known tobacco reconstitution processes whereby tobacco remnants are combined and configured substantially into a sheet-like form. An example method of manufacture of reconstituted tobacco is provided in U.S. Pat. No. 7,900,639 to Perfetti, which is incorporated by reference.

In some embodiments, the flavor material can include one or more flavorants. As used herein, reference to a "flavorant" is intended to refer to compounds or components that can be present in a flavor material (e.g., a flavor liquid) and that can be delivered to a user and which impart a sensory experience in terms of taste and/or aroma. Example flavorants include, but are not limited to, vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, rosemary, hibiscus, rose hip, yerba mate, guayusa, honeybush, rooibos, yerba santa, bacopa monniera, gingko biloba, withania somnifera, cinnamon, sandalwood, jasmine, cascarilla, cocoa, licorice, and flavorings and flavor packages of the type and character traditionally used for the flavoring of cigarette, cigar, and pipe tobaccos, as well as any combination of the foregoing flavors. Syrups, such as high fructose corn syrup, also can be employed. Example plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. The selection of such further components are variable based upon factors such as the sensory characteristics that are desired for the smoking article, and the present disclosure is intended to encompass any such further components that are readily apparent to those skilled in the art of tobacco and tobacco-related or tobacco-derived products. See, e.g., Gutcho, Tobacco Flavoring Substances and Methods, Noyes Data Corp. (1972)

and Leffingwell et al., Tobacco Flavoring for Smoking Products (1972), the disclosures of which are incorporated herein by reference in their entireties. For other examples of flavoring materials that may be suitable for the products disclosed, see, for example, US Pat. Appl. Pub. Nos. 2002/0162562 to Williams; 2002/0162563 to Williams; 2003/0070687 to Atchley et al.; 2004/0020503 to Williams, 2005/0178398 to Breslin et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0029117 to Mua et al.; 2008/0173317 to Robinson et al.; and 2008/0209586 to Neilsen et al., each of which is incorporated herein by reference.

It should be noted that reference to a flavorant should not be limited to any single flavorant as described above, and may, in fact, represent a combination of one or more flavorants. Moreover, when multiple layers and/or types of flavor substrates as disclosed herein are utilized, different flavor materials may be utilized on different layers and/or types of flavor substrates. For example, a flavor substrate formed of two layers may include different flavor materials on the two different layers.

In one or more embodiments, at least a portion of the flavor material may be provided within one or more breakable capsules, which may be included in the elongated flavor substrate 100 of the flavor delivery device 50. The one or more breakable capsules can independently carry a payload incorporating one or more flavor material(s) as discussed above. The flavor material can be released from the breakable capsule by any suitable action, such as by, for example, compression of the elongated flavor substrate, or by twisting, bending, or folding all or a portion of the flavor delivery device 50 or any other method to release the flavor from the breakable capsule. If desired, the one or more breakable capsule(s) thus can be formed from a material that is configured to rupture during use, for example, due to contact by vapor phase materials in an aerosol and/or due to an increase in temperature associated with the passage of an aerosol. The breakage of the capsule(s) acts to release the contents that are contained and sealed therein. Release of the contents achieves the intended benefit of action of certain of those contents, whether that benefit results from flavoring, scenting, cooling, or moistening the aerosol.

The breakable capsule(s) can have any desired shape, such as oval, spherical, or any other possible geometries. The breakable capsule can possess a rigid outer shell, such as a gelatin outer shell that surrounds an internal payload. Suitable capsules are commercially available from Mane Aromatic Flavors, located in Nice, France as gelatin encapsulated mixtures of medium chain triglycerides and flavor agents. The designations of a number of flavor capsules that are available from Mane Aromatic Flavors are: Spearmint, E209123; Cinnamon, E0303392; Russian Tea, E0303386; Lemon, E127382; and Menthol, E127384. Such representative breakable capsules have diameters of about 3.5 mm and about 4 mm. The outer shell of the breakable capsule is preferably constructed of a food grade gelatin derived from bovine, piscine or porcine stock. A wide variety of gelatins may be used, and the selection of a gelatin for the capsule outer surface is considered a matter of design choice to those of ordinary skill in the art. See, Kirk-Othmer, *Encyclopedia of Chemical Technology*, (4th Ed.) 12, 406-416 (1994), which is incorporated herein by reference.

Multiple breakable capsules can be accommodated in the elongated substrate 100 of the flavor delivery device 50. These capsules can contain the identical flavor material or different flavor material to either boost the flavor or to produce a different flavor. The capsules can be positioned at different spots in the elongated flavor substrate so that the flavor material is released at different times. The multiple breakable capsules can be positioned in the same spot in the elongated flavor substrate 100. For example, multiple breakable capsules can have significant different sizes or different geometries, including spherical or oval, so that at the flavor material contained in the breakable capsule with the larger diameter. For example, the user may break a first capsule with a press or compression of the flavor substrate to release a first flavor. At a later time, the user by perform a second press or compression to break a second breakable capsule containing flavor material. The second capsules may have a smaller diameter than the first capsule so that the first capsule breaks with less pressure applied relative to the pressure required to break the smaller capsules. The second press can be done later and on demand by the user in order to boost or extend the flavor from the first capsule.

The flavor delivery device 50 can include breakable capsules having diameters of at least about 1 mm, typically at least about 2 mm, and often at least about 3 mm. Typically, a breakable capsule may have diameters that do not exceed about 6 mm, often do not exceed 5 mm, and frequently do not exceed about 4.5 mm. Certain preferred breakable capsules have diameters in the range of about 3 mm to about 5 mm in diameter, and certain highly preferred breakable capsules are approximately 4.5 mm in diameter.

In one or more embodiments, a flavor delivery device 50 may further include an outer sleeve 125 substantially surrounding an outer perimeter of the elongated flavor substrate 100. The outer sleeve 125 can be provided so that it is substantially circumscribing the flavor substrate(s). Preferably, the outer sleeve 125 is present substantially along the complete longitudinal length L of the flavor substrate 100. It is understood, however, that the outer sleeve 125 may be present only along a partial length of the elongated flavor substrate 100, such as only along about a mid-section of the longitudinal length of the flavor substrate or only proximate one end of the flavor substrate. As non-limiting examples, the outer sleeve 125 can be in the form of a sheet that can be substantially wrapped around the substrate or combination of substrates, and the wrapped sheet can be glued, stitched, welded, or otherwise attached to one or more of the substrate(s) and/or to itself. As a further example, the outer sleeve 125 can be provided substantially in the form of a tube, straw, or the like, and can be slid around the substrate (s), or the substrate(s) may be positioned into the tube. The outer sleeve 125 can vary in thickness, and the thickness can be substantially constant along the complete length thereof or may vary. In some embodiments, the outer sleeve can have a thickness of about 25 microns to about 2 mm, about 50 microns to about 1 mm, or about 100 microns to about 750 microns. In further embodiments, a substantially thicker material may be used.

In some embodiments, the outer sleeve 125 that surrounds an outer perimeter of an elongated flavor substrate 100 may be formed at least in part from one or more polymeric materials such as polyether, polyester, polypropylene, polylactic acid (PLA), nylon or a combination thereof. For example, the outer sleeve 125 may be formed at least partially from fibers formed from any of the foregoing materials alone or in one or more combinations. Likewise, any one or more of the foregoing materials may be expressly excluded from use in one or more embodiments of the disclosure. The outer sleeve particularly may be formed from a biodegradable material. In other examples, the outer sleeve may be formed of different types of materials than a polymeric material. For example, in some embodiments, the outer sleeve can be formed of paper foil, filter paper, ceramics, aluminum, or any combinations thereof. Likewise, combinations of polymeric materials and non-polymeric materials may also be used. In one or more embodiments, the outer sleeve 125 may particularly be adapted or configured to substantially prevent or resist passage of any flavor material therethrough for an extended period of time (e.g., up to a time of about 6 months, about 1 year, or about 2 years) under ambient conditions. Thus, the outer sleeve 125 may be substantially impermeable to one or both of aqueous liquids and oils, at least for a minimum time as noted above.

Figure 5:
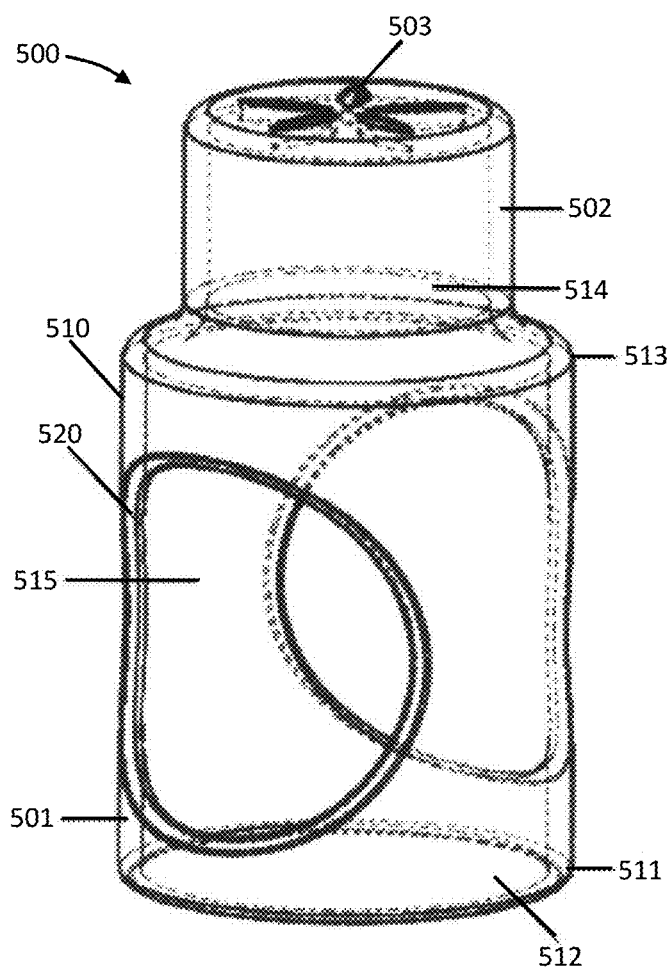
FIG. 5 is a frontal view of an example flavor delivery device comprising an outer housing showing a body and a mouth portion.

A flavor delivery device combined with a flavor substrate and flavor material can be particularly suitable according to embodiments of the present disclosure for combination with other articles, such as aerosol delivery devices in a variety of forms. As such, the flavor substrate and flavor material can be provided in a form whereby the flavor substrate may be easily combinable with such further devices. For example, in some embodiments, the flavor substrate may be combinable with an outer shell that is adapted to or configured to removably or permanently retain the flavor substrate. In the embodiment represented in FIG. 5, a flavor delivery device 500 according to an example embodiment can comprise an outer housing 510 which comprises a body 501 and a mouth portion 502. The body 501 extends along a longitudinal axis between a distal end 511 and a proximal end 513, both ends including one or more openings 512 and 514, respectively. The outer housing defines a chamber 515 therein. The mouth portion 502 may be attached to the proximal end 513 of the body portion 501 and may include one or more openings 503 formed therein. The mouth portion 502 thus may be permanently attached to the body portion 501, removably attached (including hingedly attached), or may be co-extruded with the body portion so as to be a single, monolithic structure. The outer housing 510 can have one or more openings 520 formed within the body 501 thereof.

Figure 6:
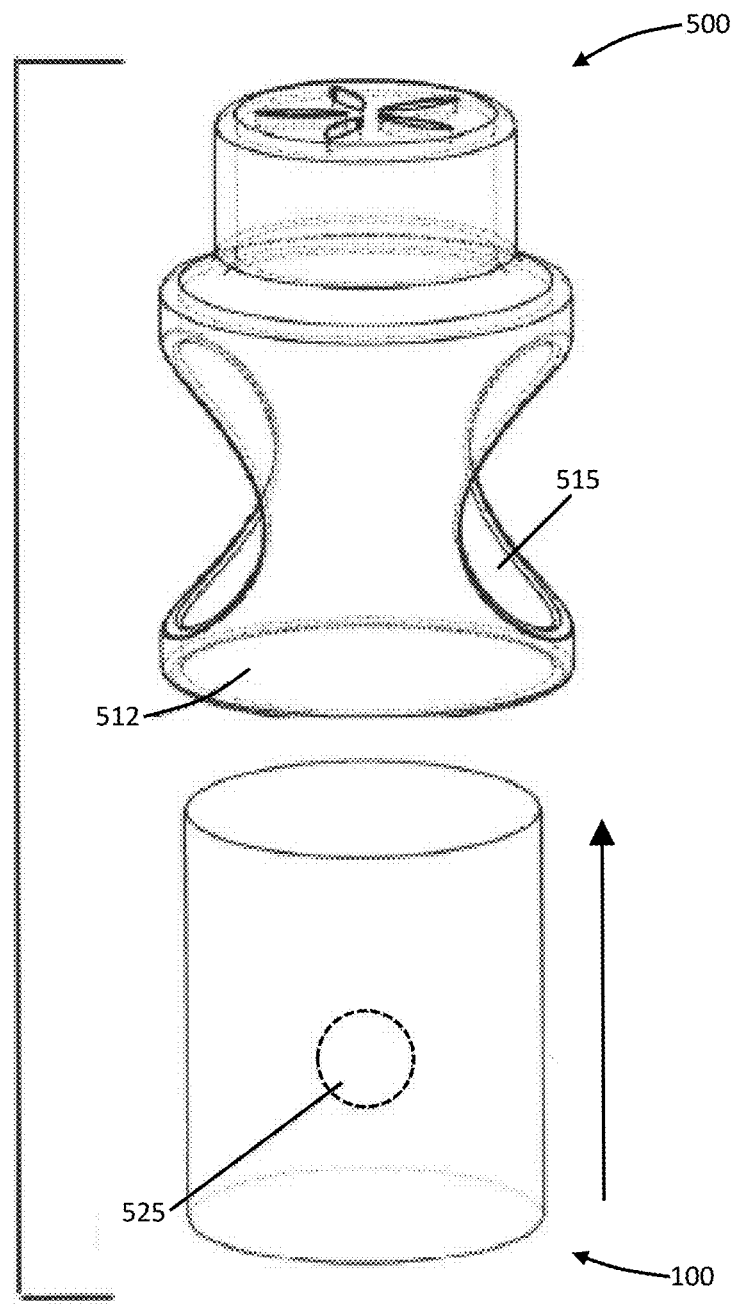
FIG. 6 represents an exploded view of an example flavor substrate circumscribed with an outer sleeve where at least one breakable capsule containing a flavorant is optionally contained inside the flavor substrate according to the present disclosure.

FIG. 6 represents an exploded view, for example, of a flavor delivery device 500 according to the present disclosure including a flavor substrate 100, which can have an outer sleeve surrounding at least a portion of the flavor substrate. As illustrated, at least one breakable capsule 525 containing a flavorant is optionally contained inside the flavor substrate 100. The flavor substrate 100 may include a flavor material therein, and such flavor material may be the same or different as the flavor material present in the at least one breakable capsule 525. Alternatively, the flavor substrate may exclude any flavor material except for the flavor material that is present inside the at least one breakable capsule 525. The flavor substrate 100 can be positioned inside chamber 515 of the outer housing 510. Once present inside chamber 515 of the outer housing 510, the flavor material present in the flavor substrate 100 and/or the at least one breakable capsule 525 can be released by passage of a stream, such as an aerosol stream, therethrough. The breakable capsule 525, for example, may be ruptured by compression of the elongated flavor substrate 100, or by twisting, bending, folding the flavor delivery device 500 (or only a portion thereof) or any other method to release the flavor from the breakable capsule. The elongated flavor substrate is removable and replaceable. Preferably, at least one elongated flavor substrate, for example flavor substrate 100 is positioned within the chamber 515 of the outer housing 510 such that the longitudinal axis of the at least one elongated substrate is substantially parallel with the longitudinal axis of the outer housing. The so-formed flavor delivery device 500 may then engage with a mouthend or be configured for insertion into an smoking article or similar device so that vapor or aerosol formed in the delivery device may pass through the opening 512 in the outer housing 510 of the flavor delivery device 500, and flavor material retained by, for example, the flavor substrate 100 and/or the breakable capsule(s) may become entrained in the vapor or aerosol, which then exits the flavor delivery device through the at least one opening 503 in the mouthpiece portion 502 of the flavor delivery device.

In one or more embodiments, a capsule or capsules used herein may be in the form of a microcapsule or a plurality of microcapsules, which may incorporate the flavor material. Microcapsules, for example, may be particularly useful for storage of the flavor material and then release thereof without the requirement for mechanical action. In other words, release of the flavor material from the microcapsules may be due to contact with a passing aerosol stream (e.g., via heat, moisture, or a chemical reaction that causes the microcapsules to release the flavor material). Encapsulation of the flavor material can be carried out using any suitable technique. For example, microcapsules can be formed using any of various chemical encapsulation techniques such as solvent evaporation, solvent extraction, organic phase separation, interfacial polymerization, simple and complex coacervation, in-situ polymerization, liposome encapsulation, and nanoencapsulation. Alternatively, physical methods of encapsulation could be used, such as spray coating, pan coating, fluid bed coating, annular jet coating, spinning disk atomization, spray cooling, spray drying, spray chilling, stationary nozzle coextrusion, centrifugal head coextrusion, or submerged nozzle coextrusion.

Regardless of the encapsulation methodology employed, the outer wall or shell material and solvents used to form the capsules can vary. Classes of materials that are typically used as wall or shell materials include proteins, polysaccharides, starches, waxes, fats, natural and synthetic polymers, and resins. Exemplary materials for use in the microencapsulation process used to form the microcapsules include gelatin, acacia (gum arabic), polyvinyl acetate, potassium alginate, carob bean gum, potassium citrate, carrageenan, potassium polymetaphosphate, citric acid, potassium tripolyphosphate, dextrin, polyvinyl alcohol, povidone, dimethylpolysiloxane, dimethyl silicone, refined paraffin wax, ethylcellulose, bleached shellac, modified food starch, sodium alginate, guar gum, sodium, sodium citrate, carboxymethylcellulose, hydroxypropyl cellulose, hydroxypropylmethylcellulose, sodium ferrocyanide, sodium polyphosphates, locust bean gum, methylcellulose, sodium trimetaphosphate, methyl ethyl cellulose, sodium tripolyphosphate, microcrystalline wax, tannic acid, petroleum wax, terpene resin, tragacanth, polyethylene, xanthan gum, and polyethylene glycol.

Microcapsules are commercially available, and exemplary types of microcapsule technologies are of the type set forth in Gutcho, Microcapsules and Microencapsulation Techniques (1976); Gutcho, Microcapsules and Other Capsules Advances Since 1975 (1979); Kondo, Microcapsule Processing and Technology (1979); Iwamoto et al., AAPS Pharm. Sci. Tech. 2002 3(3): article 25; U.S. Pat. No. 5,004,595 to Cherukuri et al.; U.S. Pat. No. 5,690,990 to Bonner; U.S. Pat. No. 5,759,599 to Wampler et al.; U.S. Pat. No. 6,039,901 to Soper et al.; U.S. Pat. No. 6,045,835 to Soper et al.; U.S. Pat. No. 6,056,992 to Lew; U.S. Pat. No. 6,106,875 to Soper et al.; U.S. Pat. No. 6,117,455 to Takada et al.; U.S. Pat. No. 6,482,433 to DeRoos et al.; and U.S. Pat.

No. 6,929,814 to Bouwmeesters et al.; each of which is incorporated herein by reference.

The flavor delivery device is beneficially useful for imparting a desired flavoring effect to an aerosol stream. As such, the flavor delivery device can be combined with any type of device that is configured for providing a flow of an aerosol stream. This can include, in example embodiments, an aerosol delivery device such further described herein or having different configurations of parts but intended to provide the same function of acting on an aerosol precursor liquid to form a vapor that can be entrained in a passing air stream and thus form an aerosol. For example, referring to FIG. 7, when a cartridge 404 is engaged with a power unit, a user drawing through the opening 428 at the mouthend of the cartridge will cause air to enter through the air entry 418. The air may flow through and/or around the reservoir 444 and entrain vapor that is formed by heating of aerosol precursor composition in the liquid transport element 436 by the heater 434 and thus form an aerosol that exits through the opening 428. There thus can be one or more airflow passages through the aerosol delivery device. As just described, the heater 434 can be positioned substantially within the airflow passage so that formed vapor is efficiently made available for entrainment in the air flowing through the cartridge 404.

Figure 7:
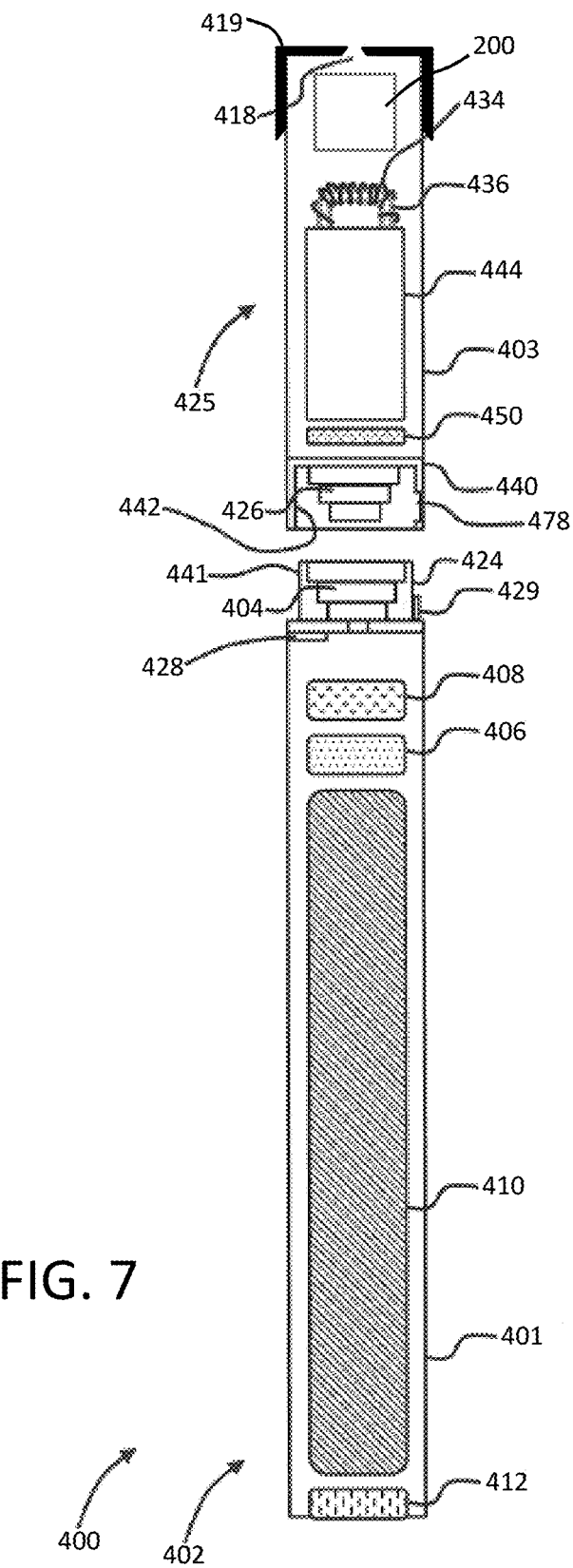
FIG. 7 is a partial cross-sectional view of an aerosol delivery device including a flavor delivery device according to the present disclosure.

In one or more embodiments, a mouthpiece 419 is provided according to the present disclosure, and the mouthpiece 419 can be adapted to or configured to connect with the mouthend of the cartridge 425 in FIG. 7. In some embodiments, a flavor delivery device 200 as described herein can be positioned substantially within the airflow passage. For example, in some embodiments, as illustrated in FIG. 7, the flavor delivery device 200 may be positioned within the cartridge 425 near a mouthend thereof. In further embodiments, the flavor delivery device 200 may be configured as otherwise described above in relation to FIG. 5 and FIG. 6 (or a similar configuration) and function essentially as a mouthpiece for an aerosol delivery device. In another embodiment, the flavor delivery device can be positioned over a mouthpiece connected to the mouthend of the cartridge housing. As such, the mouthpiece may be configured to be inserted into an end of an aerosol delivery device and/or may be configured to at least partially slide over an end of an aerosol delivery device to form a connection therewith. In one or more embodiments, the flavor delivery device 200 may be provided as a stand-alone unit that is combinable with other devices as desired to add flavor to an unflavored aerosol or provide a further flavor to be mixed with the flavor already provided by the paired device. Furthermore, the flavor delivery device can be adapted to or configured to be removably attached to one or both of the mouthend of the cartridge 425 and a mouthpiece 419 attached to the mouthend of the cartridge. Such connection may be via any one or more of a screwthread connection, a magnetic connection, a press-fit (or friction-fit) connection, or the like. As such, the flavor delivery device is replaceable by the user.

Aerosol delivery devices incorporating flavor devices of the present disclosure generally can include a number of components provided within an outer shell or body. The overall design of the outer shell or body can vary, and the format or configuration of the outer body that can define the overall size and shape of the aerosol delivery device can vary. Typically, an elongated body resembling the shape of a cigarette or cigar can be formed from a single, unitary shell; or the elongated body can be formed of two or more separable pieces. For example, an aerosol delivery device can comprise an elongated shell or body that can be substantially tubular in shape and, as such, resemble the shape of a conventional cigarette or cigar. However, various other shapes and configurations may be employed in other embodiments (e.g., rectangular or fob-shaped). Thus, an aerosol delivery device as described herein may take on any configuration desired.

In one implementation, all of the components of the aerosol delivery device are contained within one outer body, which may be defined as a housing or shell. Alternatively, an aerosol delivery device can comprise two or more shells that are joined and are separable. For example, an aerosol delivery device can comprise a control body or power unit including a shell containing one or more reusable components (e.g., a rechargeable battery and various electronics for controlling the operation of that article), and also can comprise a removably attached shell configured as a disposable portion (e.g., a disposable flavor-containing cartridge). More specific formats, configurations and arrangements of components within the single shell type of unit or within a multi-piece separable shell type of unit will be evident in light of the further disclosure provided herein. Additionally, various aerosol delivery device designs and component arrangements can be appreciated upon consideration of the commercially available electronic aerosol delivery devices.

Aerosol delivery devices of the present disclosure may comprise some combination of a power source (i.e., an electrical power source), at least one control component (e.g., means for actuating, controlling, regulating and/or ceasing power for heat generation, such as by controlling electrical current flow from the power source to other components of the aerosol delivery device), a heater or heat generation component (e.g., an electrical resistance or inductive heating element or component commonly referred to as part of an “atomizer”), and an aerosol precursor composition (e.g., commonly a liquid capable of yielding an aerosol upon application of sufficient heat, such as ingredients commonly referred to as “smoke juice,” “e-liquid” and “e-juice”), and a mouth end region or tip for allowing draw upon the aerosol delivery device for aerosol inhalation (e.g., a defined air flow path through the article such that aerosol generated can be withdrawn therefrom upon draw).

Alignment of the components within the aerosol delivery device of the present disclosure can vary. In specific implementations, the aerosol precursor composition can be located near an end of the aerosol delivery device which may be configured to be positioned proximal to the mouth of a user so as to maximize aerosol delivery to the user. Other configurations, however, are not excluded. Generally, the heating element can be positioned sufficiently near the aerosol precursor composition so that heat from the heating element can volatilize the aerosol precursor (which may itself contain one or more flavorants, medicaments, or other additives) and form an aerosol for delivery to the user. When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof, wherein such terms are also interchangeably used herein except where otherwise specified.

As noted above, the aerosol delivery device may incorporate a battery and/or other electrical power source (e.g., a capacitor) to provide current flow sufficient to provide various functionalities to the aerosol delivery device, such as powering of a heater, powering of control systems, powering of indicators, and the like. The power source can take on various implementations. In one example, the power source is able to deliver sufficient power to rapidly heat the heating element to provide for aerosol formation and power the aerosol delivery device through use for a desired duration of time. The power source may be sized to fit conveniently within the aerosol delivery device so that the aerosol delivery device can be easily handled. Additionally, in one embodiment, a power source is of a sufficiently light weight to not detract from a desirable smoking experience.

More specific formats, configurations and arrangements of components within the aerosol delivery device of the present disclosure will be evident in light of the further disclosure provided hereinafter. Additionally, the selection of various aerosol delivery device components can be appreciated upon consideration of the commercially available electronic aerosol delivery devices. Further, the arrangement of the components within the aerosol delivery device can also be appreciated upon consideration of the commercially available electronic aerosol delivery devices. Examples of commercially available products, for which the components thereof, methods of operation thereof, materials included therein, and/or other attributes thereof may be included in the devices of the present disclosure as well as manufacturers, designers, and/or assignees of components and related technologies that may be employed in the aerosol delivery device of the present disclosure are described in U.S. patent application Ser. No. 15/222,615, filed Jul. 28, 2016, to Watson et al., which is incorporated herein by reference in its entirety.

One example embodiment of an aerosol delivery device 400 illustrating components that may be utilized in an aerosol delivery device according to the present disclosure is provided in FIG. 7. As seen in the cut-away view illustrated therein, the aerosol delivery device 400 can comprise a power unit 402 and a cartridge 425 that can be permanently or detachably aligned in a functioning relationship. Engagement of the power unit 402 and the cartridge 425 can be press fit (as illustrated), threaded, interference fit, magnetic, or the like. In particular, connection components, such as further described herein may be used. For example, the power unit may include a coupler that is adapted to engage a connector on the cartridge.

In specific embodiments, one or both of the power unit 402 and the cartridge 425 may be referred to as being disposable or as being reusable. For example, the power unit may have a replaceable battery or a rechargeable battery and thus may be combined with any type of recharging technology, including connection to a typical electrical outlet, connection to a car charger (i.e., cigarette lighter receptacle), and connection to a computer, such as through a universal serial bus (USB) cable. For example, an adaptor including a USB connector at one end and a power unit connector at an opposing end is disclosed in U.S. Pat. Pub. No. 2014/0261495 to Novak et al., which is incorporated herein by reference in its entirety. Further, in some embodiments the cartridge may comprise a single-use cartridge, as disclosed in U.S. Pat. No. 8,910,639 to Chang et al., which is incorporated herein by reference in its entirety.

As illustrated in FIG. 7, a power unit 402 can be formed of a power unit shell 401 that can include a control component 406 (e.g., a printed circuit board (PCB), an integrated circuit, a memory component, a microcontroller, or the like), a flow sensor 408, a battery 410, and an LED 412, and such components can be variably aligned. Further indicators (e.g., a haptic feedback component, an audio feedback component, or the like) can be included in addition to or as an alternative to the LED. Additional representative types of components that yield visual cues or indicators, such as light emitting diode (LED) components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; U.S. Pat. Pub. No. 2015/0020825 to Galloway et al.; and U.S. Pat. Pub. No. 2015/0216233 to Sears et al.; which are incorporated herein by reference.

A cartridge 425 can be formed of a cartridge shell 403 enclosing the reservoir 444 that is in fluid communication with a liquid transport element 436 adapted to wick or otherwise transport an aerosol precursor composition stored in the reservoir housing to a heater 434. A liquid transport element can be formed of one or more materials configured for transport of a liquid, such as by capillary action. A liquid transport element can be formed of, for example, fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. The liquid transport element thus can be any material that contains an open pore network (i.e., a plurality of pores that are interconnected so that fluid may flow from one pore to another in a plurality of direction through the element).

Various embodiments of materials configured to produce heat when electrical current is applied therethrough may be employed to form the resistive heating element 434. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), titanium, platinum, silver, palladium, graphite and graphite-based materials (e.g., carbon-based foams and yarns) and ceramics (e.g., positive or negative temperature coefficient ceramics). Various other implementations of a heating element likewise may be employed. For example, a metal mesh may be positioned around a cylindrical wick, or a ribbon-like metal mesh may be positioned on a ribbon-shaped or sheet-shaped wick. For example, a heating element may be configured to heat the aerosol precursor composition disposed within a liquid transport element via radiant heating, as described in U.S. Pat. App. Pub. No. 2017/0020193, filed Dec. 3, 2015, the content of which is incorporated herein by reference. In another implementation, the heating element may be configured to heat the aerosol precursor composition via inductive heating, as described in U.S. Pat. App. Pub. No. 2017/0127722, filed Nov. 6, 2015, the content of which is incorporated herein by reference. A variety of heater components may be used in the present aerosol delivery device. In various implementations, one or more microheaters or like solid state heaters may be used. Microheaters and atomizers incorporating microheaters suitable for use in the presently disclosed devices are described in U.S. Pat. No. 8,881,737 to Collett et al., which is incorporated herein by reference.

An opening 418 may be present in the cartridge shell 403 (e.g., at the mouthend) to allow for egress of formed aerosol from the cartridge 404. Such components are representative of the components that may be present in a cartridge and are not intended to limit the scope of cartridge components that are encompassed by the present disclosure.

The cartridge 425 also may include one or more electronic components 450, which may include an integrated circuit, a memory component, a sensor, or the like. The electronic component 450 may be adapted to communicate with the control component 406 and/or with an external device by wired or wireless means. The electronic component 450 may be positioned anywhere within the cartridge 425 or its base 440.

Although the control component 406 and the flow sensor 408 are illustrated separately, it is understood that the control component and the flow sensor may be combined as an electronic circuit board with the air flow sensor attached directly thereto. Further, the electronic circuit board may be positioned horizontally relative the illustration of FIG. 7 in that the electronic circuit board can be lengthwise parallel to the central axis of the power unit. In some embodiments, the air flow sensor may comprise its own circuit board or other base element to which it can be attached. In some embodiments, a flexible circuit board may be utilized. A flexible circuit board may be configured into a variety of shapes, include substantially tubular shapes.

The power unit 402 and the cartridge 425 may include components adapted to facilitate a fluid engagement therebetween. As illustrated in FIG. 7, the power unit 402 can include a coupler 424 having a cavity 404 therein. The cartridge 425 can include a base 440 adapted to engage the coupler 424 and can include a projection 426 adapted to fit within the cavity 404. Such engagement can facilitate a stable connection between the power unit 402 and the cartridge 404 as well as establish an electrical connection between the battery 410 and control component 406 in the power unit and the heater 434 in the cartridge. Further, the power unit shell 401 can include an air entry 428, which may be a notch in the shell where it connects to the coupler 424 that allows for passage of ambient air around the coupler and into the shell where it then passes through the cavity 404 of the coupler and into the cartridge through the projection 426.

A coupler and a base useful according to the present disclosure are described in U.S. Pat. Pub. No. 2014/0261495 to Novak et al., the disclosure of which is incorporated herein by reference in its entirety. For example, a coupler as seen in FIG. 7 may define an outer periphery 441 configured to mate with an inner periphery 442 of the base 440. In one embodiment the inner periphery of the base may define a radius that is substantially equal to, or slightly greater than, a radius of the outer periphery of the coupler. Further, the coupler 424 may define one or more protrusions 429 at the outer periphery 426 configured to engage one or more recesses 478 defined at the inner periphery of the base. However, various other embodiments of structures, shapes, and components may be employed to couple the base to the coupler. In some embodiments the connection between the base 440 of the cartridge 425 and the coupler 424 of the power unit 402 may be substantially permanent, whereas in other embodiments the connection therebetween may be releasable such that, for example, the power unit may be reused with one or more additional cartridges that may be disposable and/or refillable.

The aerosol delivery device 400 may be substantially rod-like or substantially tubular shaped or substantially cylindrically shaped in some embodiments. In other embodiments, further shapes and dimensions are encompassed— e.g., a rectangular or triangular cross-section, multifaceted shapes, or the like. In particular, the power unit 402 may be non-rod-like and may rather be substantially rectangular, round, or have some further shape. Likewise, the power unit 402 may be substantially larger than a power unit that would be expected to be substantially the size of a conventional cigarette.

The reservoir 444 illustrated in FIG. 7 can be a container (e.g., formed of walls substantially impermeable to the aerosol precursor composition) or can be a fibrous reservoir. Container walls can be flexible and can be collapsible. Container walls alternatively can be substantially rigid. A container reservoir may be referred to as a tank. Moreover, a fibrous material may be provided in at least a portion of a container. In example embodiments, the reservoir 444 can comprise one or more layers of nonwoven fibers substantially formed into the shape of a tube encircling the interior of the cartridge shell 403. An aerosol precursor composition can be retained in the reservoir 444. Liquid components, for example, can be sorptively retained by the reservoir 444 (i.e., when the reservoir 444 includes a fibrous material). The reservoir 444 can be in fluid connection with a liquid transport element 436. The liquid transport element 436 can transport the aerosol precursor composition stored in the reservoir 444 via capillary action to the heating element 434 that is in the form of a metal wire coil in this embodiment. As such, the heating element 434 is in a heating arrangement with the liquid transport element 436.

In use, when a user draws on the article 400, airflow is detected by the sensor 408, the heating element 434 is activated, and the components for the aerosol precursor composition are vaporized by the heating element 434. Drawing upon the mouthend of the article 400 causes ambient air to enter the air entry 418 and pass through the cavity 404 in the coupler 424 and the central opening in the projection 426 of the base 440. In the cartridge 425, the drawn air combines with the formed vapor to form an aerosol. The aerosol is whisked, aspirated, or otherwise drawn away from the heating element 434 and out the mouth opening 428 in the mouthend of the article 400.

An input element may be included with the aerosol delivery device. The input may be included to allow a user to control functions of the device and/or for output of information to a user. Any component or combination of components may be utilized as an input for controlling the function of the device. For example, one or more pushbuttons may be used as described in U.S. Pub. No. 2015/0245658 to Worm et al., which is incorporated herein by reference. Likewise, a touchscreen may be used as described in U.S. patent application Ser. No. 14/643,626, filed Mar. 10, 2015, to Sears et al., which is incorporated herein by reference. As a further example, components adapted for gesture recognition based on specified movements of the aerosol delivery device may be used as an input. See U.S. Pub. 2016/0158782 to Henry et al., which is incorporated herein by reference.

In another aspect, the disclosure can be directed to kits that provide a variety of components as described herein. For example, a kit can comprise a control body with one or more cartridges. A kit further can comprise a control body with one or more charging components. A kit further can comprise a control body with one or more batteries. A kit further can comprise a control body with one or more cartridges and one or more charging components and/or one or more batteries. In further embodiments, a kit can comprise a plurality of cartridges. A kit further can comprise a plurality of cartridges and one or more batteries and/or one or more charging components. The kits further can include a case (or other packaging, carrying, or storage component) that accommodates one or more of the further kit components. The case could be a reusable hard or soft container. Further, the case could be simply a box or other packaging structure. In still further embodiments, the disclosed kits can comprise one or more components of a flavor delivery device as described herein. For example, the kit may comprise one or a plurality of outer housings and one or a plurality of flavor substrates. Likewise, a kit may comprise one or more containers of an e-liquid that may be combinable with the flavor substrate. Further, the outer housing(s), substrate(s) and container(s) of e-liquid may be included in any combination with further kit components noted above.

The foregoing description of use of the device can be applied to the various implementations described herein through minor modifications, which can be apparent to the person of skill in the art in light of the further disclosure provided herein. The above description of use, however, is not intended to limit the use of the article but is provided to comply with all necessary requirements of disclosure of the present disclosure.

Many modifications and other implementations of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

What is claimed is:

1. A flavor delivery device comprising:
 at least one elongated flavor substrate formed of a porous material and extending along a longitudinal axis between a first end and an opposing second end, the at least one elongated flavor substrate being free of tobacco;
 a flavor material included within the elongated flavor substrate; and
 an outer sleeve substantially surrounding an outer perimeter of the at least elongated flavor substrate without covering the first end or the opposing second end of the at least one elongated flavor substrate, the outer sleeve being substantially impermeable to the flavor material.

2. The flavor delivery device of claim 1, where one or more of the following conditions is met:
 the at least one elongated flavor substrate comprises one or more rods;
 the at least one elongated flavor substrate comprises one or more tubes;
 the at least one elongated flavor substrate is in the form of a pleated sheet;
 the at least one elongated flavor substrate is in the form of a gathered sheet;
 the at least one elongated flavor substrate is in the form of a rolled sheet.

3. The flavor delivery device of claim 1, wherein the porous material forming the at least one elongated flavor substrate is a polymeric material.

4. The flavor delivery device of claim 3, wherein the polymeric material is selected from a group consisting of polyethylene, polypropylene, polyether, polyester, polylactic acid (PLA), cellulose acetate, nylon, ceramics, or any combinations thereof.

5. The flavor delivery device of claim 1, where the outer sleeve is made out of material selected from a group consisting of silicone, polyether, polyester, polypropylene, polylactic acid (PLA), nylon, or any combination thereof.

6. The flavor delivery device of claim 1, where the at least one elongated flavor substrate is formed by a plurality of layers.

7. The flavor delivery device of claim 6, where each layer comprises materials with different densities.

8. The flavor delivery device of claim 6, where each layer in the plurality of layers is configured to release the flavor material at a different rate.

9. The flavor delivery device of claim 6, where each layer in the plurality of layers comprises a different flavor material.

10. The flavor delivery device of claim 1, where the at least one elongated flavor substrate is formed from a plurality of fibers.

11. The flavor delivery device of claim 10, where at least a portion of the plurality of fibers are sheath core fibers.

12. The flavor delivery device of claim 11, where the sheath is a porous material and where the flavor material is included in the core.

13. The flavor delivery device of claim 1, where at least a portion of the flavor material is provided within a breakable capsule.

14. The flavor delivery device of claim 13, where the device includes a plurality of the breakable capsules.

15. The flavor delivery device of claim 14, where the plurality of breakable capsules comprises capsules of at least two significantly different sizes.

16. A cartridge for an aerosol delivery device, the cartridge comprising:
 a cartridge housing having a mouthend;
 a reservoir including an aerosol precursor composition;
 a heater adapted to vaporize the aerosol precursor composition; and
 a flavor delivery device according to claim 1.

* * * * *